(12) United States Patent
Vorwerk et al.

(10) Patent No.: US 9,481,498 B2
(45) Date of Patent: Nov. 1, 2016

(54) SEALING LIP FOR USE WITH A VIEWING WINDOW

(71) Applicant: KHS GmbH, Dortmund (DE)

(72) Inventors: Jürgen Vorwerk, Mörsdorf (DE); Thomas Niehr, Bad Münster am Stein Ebernburg (DE); Marcel Scheufen, Bad Kreuznach (DE)

(73) Assignee: KHS GmbH, Dortmund (DE)

( * ) Notice: Subject to any disclaimer, the term of this patent is extended or adjusted under 35 U.S.C. 154(b) by 0 days.

(21) Appl. No.: 14/763,272

(22) PCT Filed: Jan. 22, 2014

(86) PCT No.: PCT/EP2014/000162
§ 371 (c)(1),
(2) Date: Jul. 24, 2015

(87) PCT Pub. No.: WO2014/124727
PCT Pub. Date: Aug. 21, 2014

(65) Prior Publication Data
US 2015/0360835 A1    Dec. 17, 2015

(30) Foreign Application Priority Data

Feb. 12, 2013  (DE) .................. 10 2013 101 384

(51) Int. Cl.
*B65D 53/06*    (2006.01)
*A61L 2/26*    (2006.01)
(Continued)

(52) U.S. Cl.
CPC .............. *B65D 53/06* (2013.01); *A61L 2/26* (2013.01); *B65D 25/54* (2013.01); *E06B 7/23* (2013.01); *E06B 7/231* (2013.01); *A61L 2202/121* (2013.01)

(58) Field of Classification Search
CPC ......... B65D 53/06; B65D 25/54; E06B 7/23; E06B 7/231; A61L 2/26; A61L 2202/121
See application file for complete search history.

(56) References Cited

U.S. PATENT DOCUMENTS

| 1,092,476 | A | * | 4/1914 | Drummond | E06B 1/702 52/204.5 |
| 4,930,257 | A | * | 6/1990 | Windgassen | E06B 1/325 49/400 |
| 7,107,736 | B2 | * | 9/2006 | Barnard | E06B 3/5892 52/204.54 |

FOREIGN PATENT DOCUMENTS

| DE | 16 83 650 | 11/1969 | |
| DE | 3203253 A1 | * 8/1983 | ......... E06B 3/26303 |

(Continued)

*Primary Examiner* — Jeanette E Chapman
(74) *Attorney, Agent, or Firm* — Occhiuti & Rohlicek LLP (57) ABSTRACT

An apparatus for permitting inspection of container processing includes a one-piece elastic peripheral lip seal that seals a transition between a window and a mounting frame. In its un-deformed state, the lip-seal, which has first and second strip-shaped lip-sections, has an at least partially sickle-shaped cross-section in its un-deformed state. Both lip sections extend outward toward respective first and second edges, the second edge being a sealing edge. A thickness of the second lip-section decreases towards the sealing edge. The lip sections curve around an axis oriented along a longitudinal direction of the lip seal. The first lip-section defines a concave curve along a first surface of the lip seal, and the second lip-section defines a convex curve along the first surface.

13 Claims, 5 Drawing Sheets

(51) Int. Cl.
    *E06B 7/23*    (2006.01)
    *B65D 25/54*   (2006.01)

(56) References Cited

FOREIGN PATENT DOCUMENTS

| DE | 3419452 A1 | * | 11/1985 | ............... E06B 7/23 |
| DE | 35 24 124 | | 1/1986 | |
| DE | 90 15 034 | | 11/1991 | |
| DE | 10235374 | | 2/2004 | |
| DE | EP2179746 A1 | * | 4/2010 | ............... A61L 2/26 |
| DE | 102009011147 A1 | * | 9/2010 | ............... A61L 2/26 |
| EP | 1 614 850 | | 1/2006 | |
| GB | 1266937 A | * | 3/1972 | ............ E06B 3/308 |
| GB | 2273960 | | 7/1994 | |
| JP | 05263568 A | * | 10/1993 | |
| JP | 06073952 A | * | 3/1994 | |
| WO | WO2009/003924 | | 1/2009 | |

* cited by examiner

SEALING LIP FOR USE WITH A VIEWING WINDOW

RELATED APPLICATIONS

This application is the national stage under 35 USC 371 of international application PCT/EP2014/000162 filed on Jan. 22, 2014, which claims the benefit of the Feb. 12, 2013 priority date of German application DE 102013101384.8, the contents of which are herein incorporated by reference.

FIELD OF INVENTION

The invention relates to a viewing window for inspecting the interior of a clean room and a seal for sealing the window.

BACKGROUND

Particularly in the beverage industry, increasingly high demands are placed on hygiene when treating containers, particularly when filling and closing containers under sterile and/or aseptic conditions. Corresponding treatment machines or devices therefore often require that, during the treatment, the container, or at least that region of the container that has the container opening, be placed in a clean chamber that separates it from a non-sterile surrounding environment.

To allow access for maintenance and repair work, and to observe the container treatment processes, for example the filling and closing process, it is customary to provide viewing windows in the separating walls that form an enclosure. It is important that a substantial portion of these separating walls be transparent.

The separating walls have mounting frames and panes. Although the panes are removable from the mounting frame, they are tightly connected to it using permanently elastic pane seals. The pane seals are connected to the mounting frame by adhesive bonds or by using special clamping profiles.

The pane seals and the sealing arrangements that use those seals for sealing a viewing window to a mounting frame are critical. These seals help ensure the sterility of the clean chamber.

Known pane seals and sealing arrangements have uncontrolled features, such as nooks, gaps, undercuts, and pockets. These uncontrolled features regularly form the starting point for contamination and/or soiling. Such features have thus far been unavoidable in the region of the pane seals, especially on the side of the pane seal that faces the clean chamber.

Pocket formation is encouraged by exposure to chemicals, high temperatures, and intensive air-flow. The risk of pocket formation increases over time, as relentless attacks on the adhesive bonds degrade the clamping effect intrinsic to the seal.

Adhesive bonds with clamping profiles for retaining the pane seals require a laborious and time-consuming assembly procedure. This is also true for assembly of seals that require adhesive bonds, which moreover are undesirable when replacing defective viewing windows or defective seals.

Known lip seals have a U-shaped profile for attachment. In these known lip seals, the U-shaped profile straddles the aperture edge surrounding an aperture of an enclosure in much the same way a rider straddles his horse. A reliable and, in particular, permanently gap-free attachment of the lip seal to the enclosure cannot be achieved with this seal.

Another known seal has an inflatable sealing profile that seals a transition between a door leaf and a frame surrounding the door leaf. When inflated, the seal develops a sickle-shaped sealing section that bears against the door leaf. These known sealing profiles are neither intended nor suitable for the peripheral sealing of an aperture closure and viewing window of an enclosure that forms a clean chamber.

SUMMARY

Among the objects of the invention is that of providing a seal that avoids the aforementioned disadvantages are avoided. Such a seal permits pane sealing in enclosures in a way that avoids undesired nooks, gaps and/or undercuts, particularly also on the side that faces the clean chamber or sterile chamber of the enclosure.

The lip seal according to the invention and/or a sealing arrangement comprising the seal optimally meet the high demands even in the case of enclosures for sterile chambers or clean chambers. Due to the special shape of the lip seal, the possibility of incorrect seal mounting is also avoided or minimized.

For attachment purposes, the lip seal, which preferably has a solid profile, is clamped with a first lip seal section thereof in an elastically deformed manner between two parallel or substantially parallel clamping surfaces. This manner of clamping is able to avoid uncontrolled nooks, gaps, undercuts, and/or pockets that could form the starting point for contamination and/or soiling and to do so even in the region of the lip seal.

In one aspect, the invention features an apparatus for permitting inspection of container processing. Such an apparatus includes a one-piece lip seal made from an elastic material, a first structure, a second structure, and a transition between the first structure and the second structure, the transition being sealed by the lip seal. The lip seal has strip-shaped first and second lip-sections that extend outward towards corresponding first and second edges, the second edge being a sealing edge. A thickness of the second lip-section decreases towards the sealing edge. In an undeformed state thereof, the lip-seal has an at least partially sickle-shaped cross-section, with the first and second lip-sections being curved around an axis oriented along a longitudinal direction of the lip seal. The lip seal comprises a first surface, with the first lip-section defining a concave curve along the first surface, and the second lip-section defining a convex curve along the first surface. The first structure is an aperture frame or a mounting frame. The second structure is either an aperture closure, a viewing window, or a viewing window of a clean chamber for treatment of a container. Container treatment is either sterile treatment of the container or aseptic treatment of the container. The elastic material is either rubber-elastic material, permanently elastic material, a rubber-elastic, permanently elastic plastic, or silicone.

Some embodiments further include a sealing arrangement having first and second clamping surfaces, and an installation gap between them. The first lip-section is disposed in the installation gap, clamped between the first and second clamping surfaces. As a result of being clamped, the first lip-section sustains elastic deformation. The second lip-section protrudes from the clamping surfaces, and the sealing edge bears against the second structure, with the concave surface facing the second structure. Among these embodiments are those in which the first structure comprises a mounting frame that defines a mounting-frame aperture, and the second structure comprises a viewing window that comprises a pane that closes the mounting-frame aperture. The seal is a peripheral lip-seal that seals a transition between the pane and the mounting frame. Such embodiments also include means for retaining the pane on the mounting frame.

In some embodiments, the lip seal is arranged with a convex side thereof facing the clean chamber.

In others, the first structure comprises first and second frame-parts that define an installation gap therebetween.

Also among the embodiments are those in which the first structure forms an inner side facing towards the clean chamber and an outer side facing towards surroundings thereof. In these embodiments, an inner side of the second structure faces an outer side of the first structure, and the inner side of the second structure is spaced apart from the outer side of the first structure.

In yet other embodiments the first structure comprises first and second frame-parts, and the first lip-section is elastically deformed to 70%-80% of its original thickness as a result of being clamped between the first and second frame-parts.

In still other embodiments, the sealing edge bears against an inner side of the second structure at a distance from a peripheral edge of the second structure, and the sealing edge is disposed at a distance from an inner edge of the second structure.

Additional embodiments include those in which the second structure and the lip seal define an obtuse angle that opens into the clean chamber.

In other embodiments, as a result of a shape of the lip seal and elastic deformation thereof, the first lip-section presses against a clamping surface in the clean chamber.

Yet other embodiments include a plurality of clamping screws, and a plurality of female thread pieces. In theses embodiments, the first structure comprises first and second frame-parts, the clamping screws are disposed for clamping the first lip-section between first and second frame-parts of the first structure, and each clamping screw cooperates with a corresponding one of the female thread pieces.

In other embodiments, the second structure comprises a periphery, and an outer side. The apparatus in these embodiments further comprises catches, and supporting elements. The catches bear against the outer side of the second structure. The supporting elements are provided on the first structure, and the periphery of the second structure bears against the supporting elements.

Other embodiments include an enclosure for defining the clean chamber and separating the clean chamber from surroundings thereof, wherein containers are aseptically treated within the enclosure, wherein the enclosure comprises a wall, and wherein the wall comprises the second structure.

In another aspect, the invention features an apparatus for permitting inspection of container processing includes a one-piece elastic peripheral lip seal that seals a transition between a window and a mounting frame. In its un-deformed state, the lip-seal, which has first and second strip-shaped lip-sections, has an at least partially sickle-shaped cross-section in its un-deformed state. Both lip sections extend outward toward respective first and second edges, the second edge being a sealing edge. A thickness of the second lip-section decreases towards the sealing edge. The lip sections curve around an axis oriented along a longitudinal direction of the lip seal. The first lip-section defines a concave curve along a first surface of the lip seal, and the second lip-section defines a convex curve along the first surface.

As used herein a lip seal is "designed as a solid profile" when the lip seal has no recess or groove for attaching it by pushing it onto an aperture edge so that it straddles the edge in the same way that an equestrian straddles his horse.

As used herein, the adjective, "peripheral," when used in reference to a seal, means that that the lip seal or a bead formed on the seal extends around an entire periphery of a mounting frame aperture and is preferably formed in a continuous manner, i.e. without interruption.

As used herein, "container" includes packages or containers that are usually used in particular in the food sector and specifically also in the beverage sector, including receptacles, such as bottles, cans, and soft packages, for example those made from cardboard, plastic film and/or metal foil.

As used herein, "treatment machines" or "treatment devices" are machines or devices for treating and/or processing containers, including, for example and without limitation, blow molding machines for the blow-molding of containers, cleaning machines for cleaning containers, rinsing machines for rinsing containers, filling machines for filling containers, and closing machines for closing containers.

As used herein, "clean chamber" includes a clean or sterile chamber that forms an aseptic zone in which at least that region of a container that has a container opening can be treated under sterile and/or aseptic conditions.

As used herein, the expression "substantially" or "around" means deviations of +/−10%, preferably of +/−5%, from the exact value in each case, and/or deviations in the form of changes which have no impact on function.

As used herein, sterile treatment is intended to mean sterile and/or aseptic treatment.

Further developments, advantages and possible uses of the invention will become apparent from the following description of examples of embodiments and from the figures. All the features described and/or shown form in principle, per se or in any combination, the subject matter of the invention, regardless of the way in which they are combined in the claims or the way in which they refer back to one another. The content of the claims is also included as part of the description.

BRIEF DESCRIPTION OF THE FIGURES

The invention will be explained in more detail below with reference to the figures and on the basis of an exemplary embodiment. In the figures.

DETAILED DESCRIPTION

Figure 1:
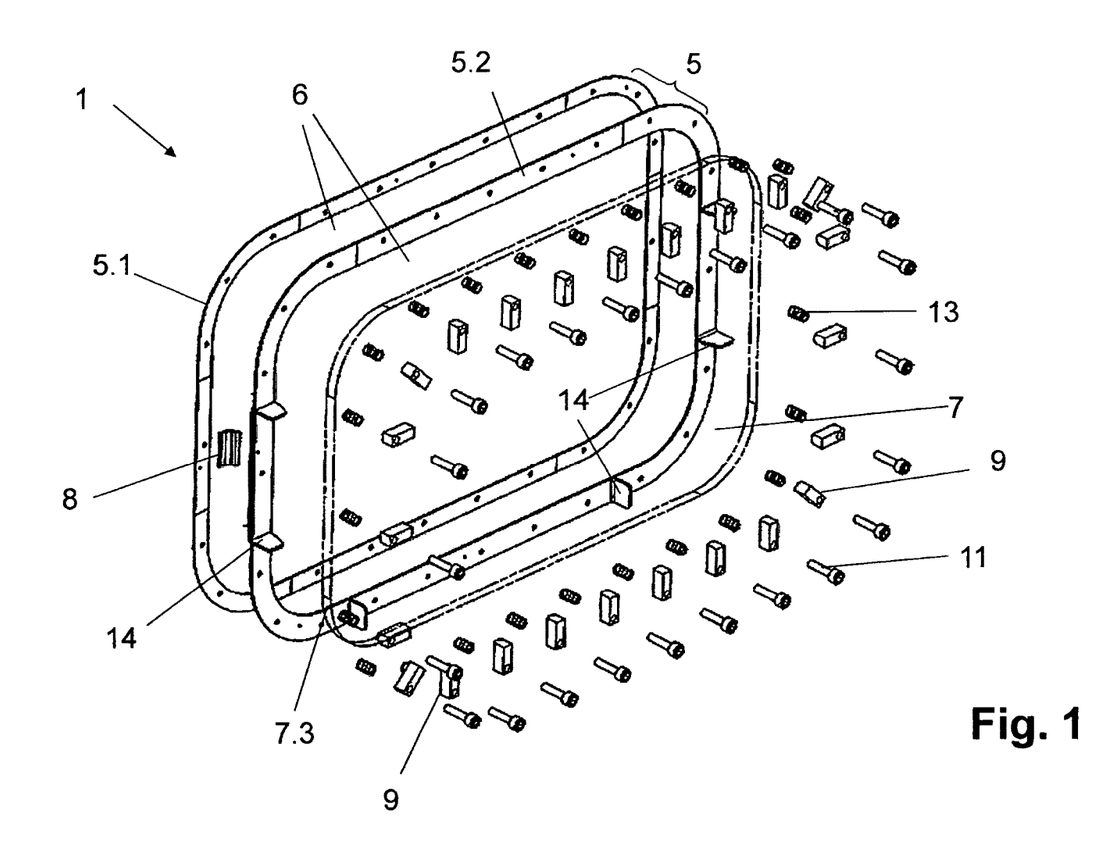
FIG. 1 shows, in an exploded view, the elements of a viewing window of an enclosure for a system for the sterile treatment of containers.
Figure 2:
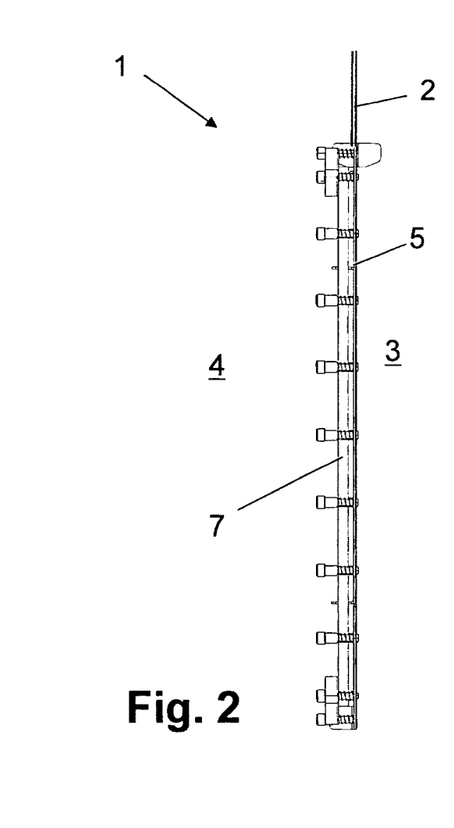
FIGS. 2 and 3 show the viewing window of FIG. 1 in the assembled state in plan view and in side view respectively.
Figure 3:
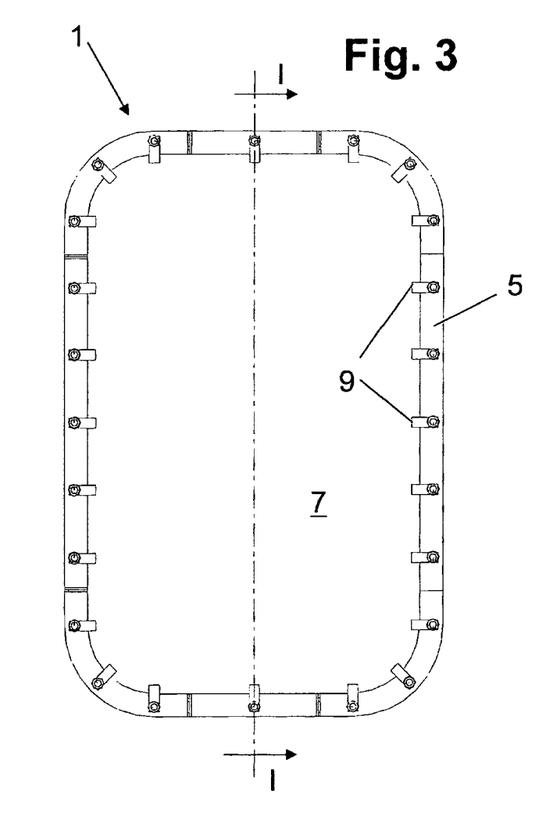
Figure 4:
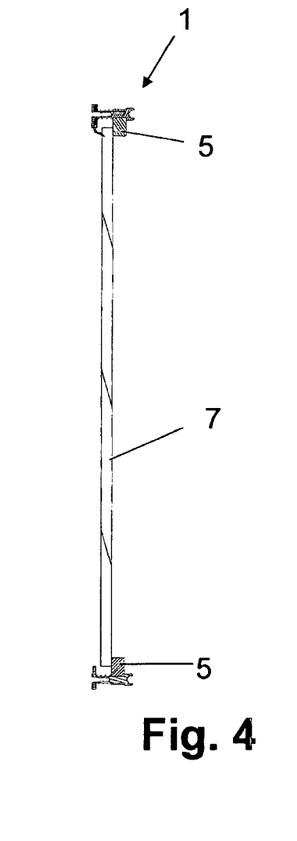
FIG. 4 shows a cross-section along the line I-I in FIG. 2.

FIG. 1 shows an exploded view of a viewing window 1 that is part of an enclosure that encloses treatment machines, devices, or units that carry out sterile treatment of containers. An example of such treatment is the sterile filling of the container with a product and closing thereof. FIGS. 2-4 show views of the viewing window 1 of FIG. 1 in assembled form.

The enclosure includes vertical separating walls, of which only one vertical separating wall 2 is shown in FIG. 2. The separating walls separate a clean chamber 3 from a non-sterile surrounding environment 4. The clean chamber 3 forms an aseptic zone in which containers are at least partly accommodated during treatment thereof. In particular, the clean chamber 3 accommodates at least a region of a container that includes the container's opening.

The viewing window 1 comprises a window frame or mounting frame 5, a pane 7, a lip seal 8, and catches 9.

The mounting frame 5 attaches, in a suitably sealed manner, to an aperture 6 in a separating wall 2. The aperture 6 is tailored to conform to the shape of the mounting frame 5.

The pane 7 is made of a transparent material that covers the aperture 6. Examples of a suitable transparent or clear material from which to make the pane 7 include glass, or plastic, including, for example, polycarbonate.

The pane 7 forms a pane inner-side 7.1 and a pane outer-side 7.2. When the pane 7 is installed, the pane inner-side 7.1 faces the clean chamber 3, and the pane outer-side 7.2 faces the surrounding environment 4.

The catches 9 hold the pane 7 on the mounting frame 5 in a removable manner. The catches 9 do so by pressing the pane 7 against the lip seal 8. Neither attachment openings in the pane 7 nor functional elements on the pane 7 are necessary for attaching the pane 7.

The lip seal 8 seals the transition between the mounting frame 5 and the pane 7. Preferably, the lip seal 8 is made a rubber-elastic or permanently elastic material, and preferably made of a food-grade rubber-elastic or permanently elastic material. An example of a suitable material is silicone. As shown in FIG. 1, the lip seal 8 is a strip that extends around the periphery of the frame 5.

Figure 6:
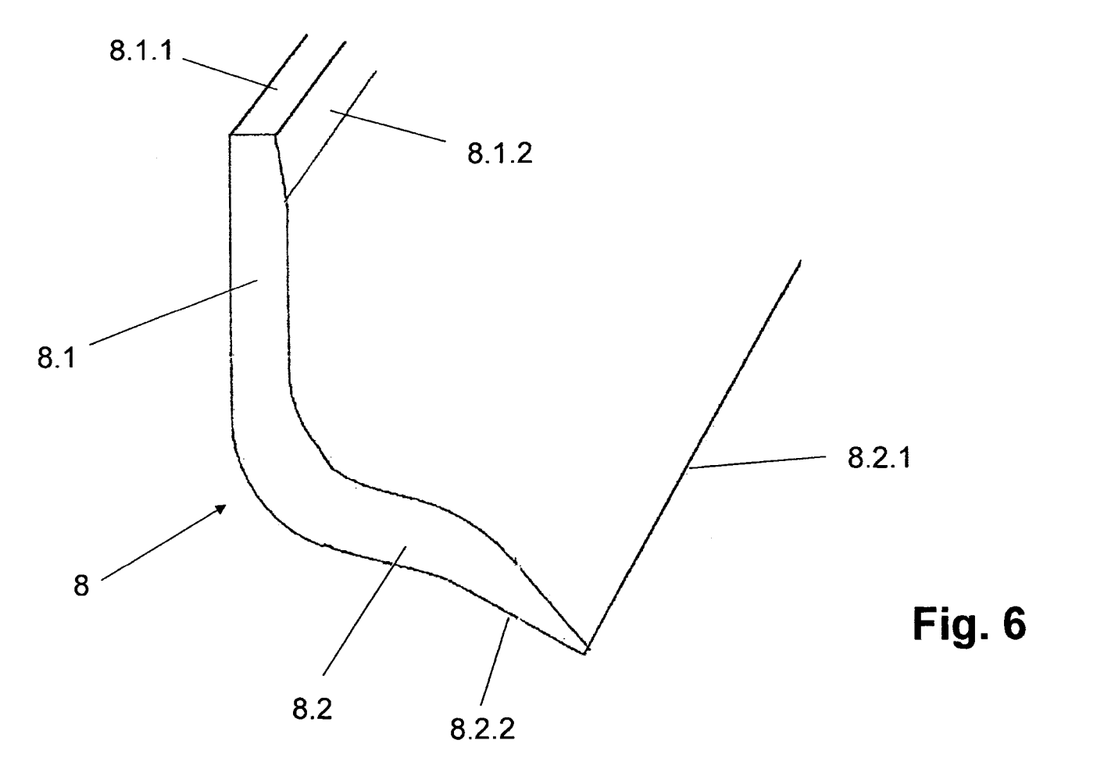
FIG. 6 shows, in a detail view, a lip seal for use on the viewing window of FIGS. 1-5.

Referring now to FIG. 6, the strip defined by the lip seal 8 has a center axis. First and second lip-sections 8.1, 8.2 extend outward from the center axis towards first and second edges 8.1.1, 8.2.1. The second edge 8.2.1 will be referred to as "the sealing edge" for reasons that will be apparent below.

In its non-deformed state, shown in FIG. 6, the lip seal 8 has a substantially sickle-shaped cross-section having an axis-of-inflection along the center axis. The thickness of the second lip-section 8.2 is greatest at the center axis and decreases as one proceeds along an axis perpendicular to the center axis toward the sealing edge 8.2.1. The thickness of the first lip-section 8.1 is likewise greatest at the center axis and stays substantially constant until reaching the chamfer 8.1.2.

In the non-deformed state shown in FIG. 6, the first and second lip-sections 8.1, 8.2 have opposite curvatures. Along a first surface of the lip 8, the first lip-section 8.1 defines a concave surface and the second lip-section 8.2 defines a convex surface. Conversely, along a second surface opposite the first surface, the first lip-section 8.1 defines a convex section and the second lip-section 8.2 defines a concave section. In both cases, the concave and convex surfaces meet at the center axis, which thus defines an axis of inflection.

Figure 5:
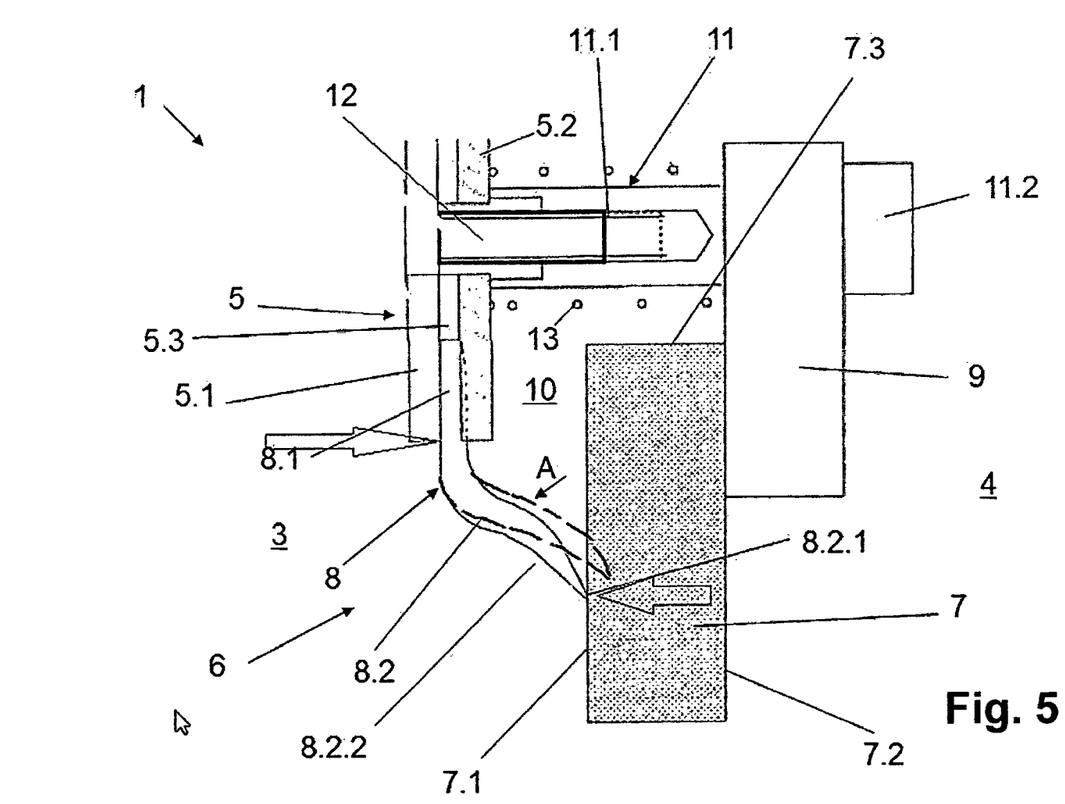
FIG. 5 shows, in an enlarged partial view and in cross-section, the frame of the viewing window of FIGS. 1-4 together with the pane closing the window aperture or frame aperture.

As shown in FIG. 5, when held on the mounting frame 5, the pane 7 is offset relative to the mounting frame 5 in the direction of the surrounding environment 4. This forms a gap 10 between the mounting frame 5 and the pane 7.

In the illustrated embodiment, the pane 7 is larger than the mounting frame aperture 6. As a result, a pane edge 7.3 of the pane 7 overlaps the mounting frame 5 in the region of the edge of the mounting frame aperture 6. The pane inner-side 7.1 thus faces towards the outer side of the mounting frame 5 across the gap 10.

In the illustrated embodiment, the mounting frame 5 comprises a first frame-part 5.1 and a second frame-part 5.2, both of which surround the mounting frame aperture 6. The first and second frame-parts 5.1, 5.2 are provided one behind the other, or one after the other in the direction of an axis oriented perpendicular to the plane of the mounting frame aperture 6. The first and second frame-parts 5.1, 5.2 are made of metal or plastic. In the case of metal frame-parts 5.1, 5.2, the metal is preferably corrosion-resistant, such as corrosion-resistant steel.

The first and second frame-parts 5.1, 5.2 clamp the first lip-section 8.1 of the lip seal 8 between them, as shown in FIG. 5. This is carried out preferably without gluing. The clamping action causes elastic deformation of the material of the lip seal 8. As a result of this elastic deformation, a clamped first lip-section 8.1 has a thickness that is only around 80%-90% of a corresponding unclamped first lip-section 8.1, as shown in FIG. 6. The spacing between the first and second frame-parts 5.1, 5.2 defines an installation gap 5.3 to accommodate the first lip-section 8.1. The width of this installation gap 5.3 is, for example, 1.8-2.2 millimeters, and preferably 2 millimeters.

Meanwhile, the second lip-section 8.2 protrudes from the installation gap 5.3 at an inner edge of the mounting frame 5 surrounding the mounting frame aperture 6 and extends into the mounting frame aperture 6. The second lip-section 8.2 is curved when the pane 7 is mounted. A chamber-side surface faces the clean chamber 3. Starting from the inner edge of the mounting frame 5, this chamber-side surface is first convex and then concave. The sealing edge 8.2.1 of the second lip-section 8.2 bears against the pane's inner-side 7.1.

In the original state of the lip seal 8, before it has been installed or pressed against the pane 7, the second lip-section 8.2, which is the section that seals the gap 10, is curved to a more pronounced extent. As a result, when the pane 7 is installed, the second lip-section 8.2 is elastically deformed along a deformation direction A. This deforms its curvature. The resulting deformation achieves a necessary pressing force of the sealing edge 8.2.1 against the pane's inner-side 7.1.

It is particularly important that the second lip-section 8.2 bear against the pane inner-side 7.1 without forming any nooks, gaps, and/or undercuts in the clean chamber 3. This is achieved in particular by the special curvature of the second lip-section 8.2 and by the fact that the lip seal's thickness tapers towards the sealing edge 8.2.1.

A distal portion 8.2.2 of the second lip-section 8.2, which has a face that faces towards the clean chamber 3, merges continuously or substantially continuously at the sealing edge 8.2.1 into a plane defined by the pane's inner side 7.1. The distal portion 8.2.2, particularly also at the sealing edge 8.2.1, defines an obtuse angle that opens towards the clean chamber 3. One side of this angle is the pane's inner side 7.1 and the other side of this angle is the distal portion 8.2.2.

A plurality of bolts 11 clamps the first lip-section 8.1 between the first and second frame-parts 5.1, 5.2. Each bolt 11 has a first bolt-end having a bolt head 11.2 thereon, a second bolt-end, and an internal thread 11.1 accessible from the second bolt-end. Clamping screws 12, or equivalently, clamping bolts are welded to the first frame-part 5.1. Each clamping screw 12 passes through a corresponding opening in the second frame-part 5.2 and engages an internal thread 11.1 of a corresponding bolt 11.

Provided on each bolt 11 is a catch oriented with its axis perpendicular to the plane of the mounting frame 5. Each catch 9 is pivotable manner. A corresponding compression spring 13 surrounds the bolt 11. The compression spring 13, which is supported against both the mounting frame 5 and the catch 9, secures the catch 9 against undesired rotation. The pane 7 bears with its pane edge 7.3 against supporting tabs 14 on the second frame-part 5.2.

Due to the special shape of the lip seal 8 and the installation thereof, the lip seal 8 is not only mechanically pressed between the first and second frame-parts 5.1, 5.2 in the installation gap 5.3, it is also optimally pressed against the important surfaces when the window is closed. In particular, the lip seal 8 is pressed with its sealing edge 8.2.1 against the pane's inner side 7.1 and with its first lip-section 8.1 pressed against the first frame-part 5.1 on the inner side of the enclosure, as indicated by the arrow B in FIG. 7.

Figure 7:
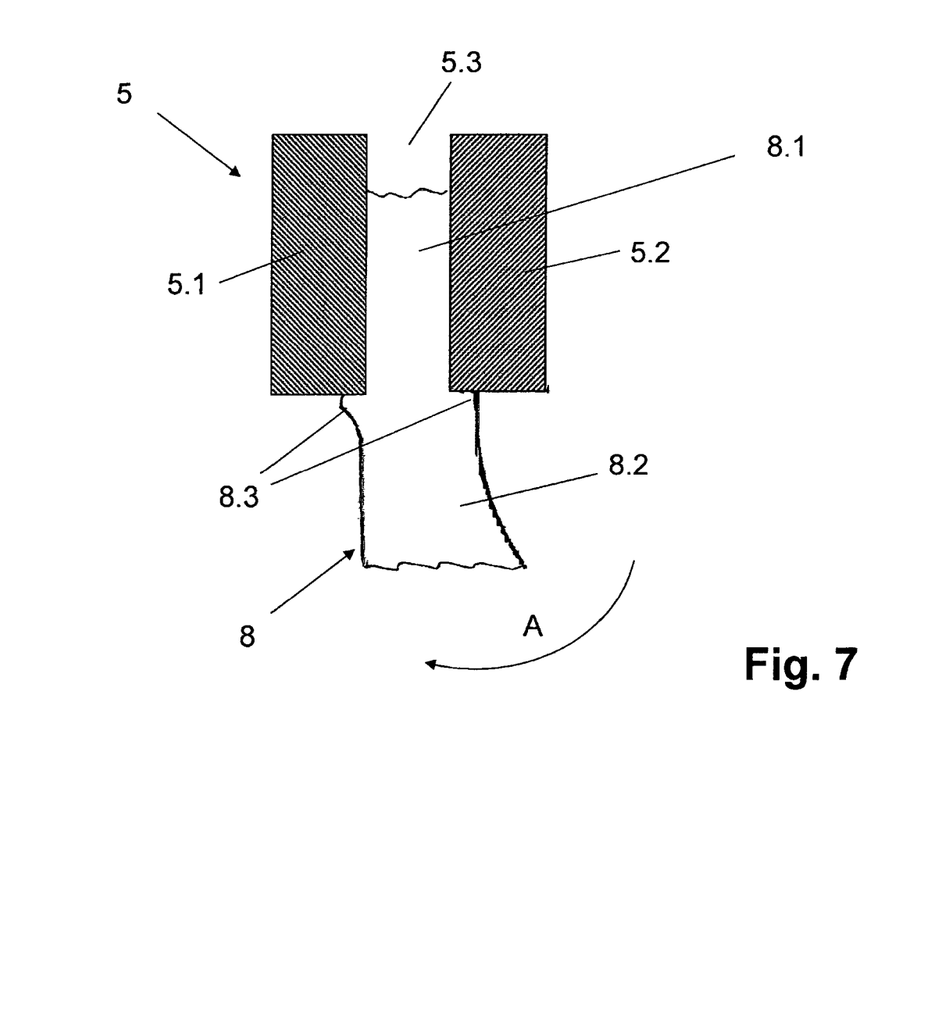
FIG. 7 shows, in an enlarged view, the transition between the lip seal section clamped in the mounting frame, thereby undergoing elastic deformation, and the unclamped, free lip seal section.

Also due to the particular shape of the lip seal 8, the second lip-section 8.2 thereof forms, at a lower, horizontal region of the peripheral seal on the inner side of the enclosure, a surface that is inclined obliquely downwards. Liquid tends to flow off this surface. This avoids having accumulation of liquid that may pose a contamination risk.

The described installation of the lip seal 8 makes it possible to attach a lip seal even with thin-walled components. Because the lip-seal 8 does not have to actually enclose these components, there is no undesired formation of pockets. ***

The peripheral lip seal 8 lies with its circumference and also with a substantial part of its first lip-section 8.1 outside of the clean chamber 3 and pressed between the first and second frame-parts 5.1, 5.2. Meanwhile, the second sealing-lip section 8.2, which forms the effective part of the lip seal 8, is free and has no effect or substantially no effect on the mounting frame 5 or the separating wall 2. As a result, the pane 7 can be mounted without causing any negative effect on the sealing action between the lip seal 8 and the mounting frame 5 or the enclosure 2.

The shape and manner of installing the lip seal 8 together reliably avoid nooks, gaps and/or undercuts in a transition region between the mounting frame 5 and the pane 7 in the clean chamber 3. In particular, the design of the lip seal 8, with its first and second lip-sections 8.1 and 8.2, and the deformation of the second lip section 8.2 when the pane 7 is mounted collectively cause a pressing action that additionally seals the transition between the lip seal 8 and the mounting frame 5. At the same time, the lip seal 8, at its sealing edge 8.2.1, bears against the pane inner side 7.1 without forming any nooks, gaps and/or undercuts. The considerable elastic deformation of the first lip-section 8.1 as it is held clamped between the first and second frame-parts 5.1, 5.2 results in a tight transition between the lip seal 8 and the mounting frame 5.

The greater total curvature of the second sealing-lip section 8.2 it its original state and the elastic alteration that it sustains when the window 7 is installed causes the sealing edge 8.2.1 to exert a high pressing force against the pane inner side 7.1.

In some embodiments, the pane's inner-side 7.1 is completely smooth and the pane's outer side 7.2 has no sealing elements or other functional elements of its own, such as, strips, etc., that could form undesired nooks, gaps, and/or undercuts.

The tension with which the first lip-section 8.1 is clamped between the first and second frame-parts 5.1, 5.2 is applied exclusively by the bolts 11 and the clamping screws 12. As a result, it is possible to achieve reproducible conditions for the installation of the lip seal 8. This also applies to the extent of the elastic deformation of the first lip-section 8.1, since the thickness of this section in the normal state is precisely predefined and the width of the installation gap 5.3 can be precisely maintained by a metal stop.

The clamping of the first lip-section 8.1 ensures a secure hold of the lip seal 8 even without using adhesives. This results in a much easier installation process.

The invention has been described above on the basis of an example of embodiment. It will be understood that numerous changes and modifications are possible without thereby departing from the inventive concept on which the invention is based.

Having described the invention, and a preferred embodiment thereof, what is claimed as new and secured by Letters Patent is:

1. An apparatus for permitting inspection of container processing, said apparatus comprising a lip seal, a first structure, a second structure, and a transition between said first structure and said second structure, wherein said lip seal seals said transition, wherein said lip seal is produced in one piece, wherein said lip seal is made from an elastic material, wherein, in an un-deformed state thereof, said lip-seal has an at least partially sickle-shaped cross-section, wherein said lip seal comprises a strip-shaped first lip-section, wherein said first lip-section extends outward to a first edge, wherein said lip seal has a strip-shaped second lip-section, wherein said second lip-section extends outward to a second edge, wherein said second edge is a sealing edge, wherein a thickness of said second lip-section decreases towards said sealing edge, wherein, in said undeformed state, said first lip-section and said second lip-section are curved around an axis oriented along a longitudinal direction of said lip seal, wherein said lip seal comprises a first surface, wherein said first lip-section defines a concave curve along said first surface, wherein said second lip-section defines a convex curve along said first surface, wherein said first structure is selected from the group consisting of an aperture frame and a mounting frame, wherein said second structure is selected from the group consisting of an aperture closure and a viewing window, and a viewing window of a clean chamber for treatment of a container, wherein treatment of a container is selected from the group consisting of sterile treatment of said container and aseptic treatment of said container, and wherein said elastic material is selected from the group consisting of a rubber-elastic material, permanently elastic material, a rubber-elastic, permanently elastic plastic, and silicone.

2. The apparatus of claim 1, further comprising a sealing arrangement, wherein said sealing arrangement comprises a first clamping surface, a second clamping surface, and an installation gap between said first clamping surface and said second clamping surface, wherein said first lip-section is disposed in said installation gap, wherein said first lip-section is clamped between said first clamping surface and said second clamping surface, wherein, as a result of being clamped, said first lip-section sustains elastic deformation, wherein said second lip-section protrudes from said clamping surfaces, and wherein said sealing edge bears against said second structure, and wherein said concave surface faces said second structure.

3. The apparatus of claim 2, wherein said first structure comprises a mounting frame, wherein said second structure comprises a viewing window, wherein said mounting frame defines a mounting-frame aperture, wherein said viewing window comprises a pane that closes said mounting-frame aperture, wherein said seal is a peripheral lip-seal that seals a transition between said pane and said mounting frame, and wherein said apparatus further comprises means for retaining said pane on said mounting frame.

4. The apparatus of claim 1, wherein said lip seal is arranged with a convex side thereof facing said clean chamber.

5. The apparatus of claim 1, wherein said first structure comprises first and second frame-parts that define an installation gap therebetween.

6. The apparatus of claim 1, wherein said first structure forms an inner side facing towards said clean chamber and an outer side facing towards surroundings thereof, wherein an inner side of said second structure faces an outer side of said first structure, and wherein said inner side of said second structure is spaced apart from said outer side of said first structure.

7. The apparatus of claim 1, wherein said first structure comprises first and second frame-parts, and wherein said first lip-section is elastically deformed to 70%-80% of its original thickness as a result of being clamped between said first and second frame-parts.

8. The apparatus of claim 1, wherein said sealing edge bears against an inner side of said second structure at a distance from a peripheral edge of said second structure, and wherein said sealing edge is disposed at a distance from an inner edge of said second structure.

9. The apparatus of claim 1, wherein said second structure and said lip seal define an angle that opens into said clean chamber, and wherein said angle is obtuse.

10. The apparatus of claim 1, wherein as a result of a shape of said lip seal and elastic deformation thereof, said first lip-section presses against a clamping surface in said clean chamber.

11. The apparatus of claim 1, further comprising a plurality of clamping screws, and a plurality of female thread pieces, wherein said first structure comprises first and second frame-parts, wherein said clamping screws are disposed for clamping said first lip-section between first and second frame-parts of said first structure, and wherein each clamping screw cooperates with a corresponding one of said female thread pieces.

12. The apparatus of claim 1, wherein said second structure comprises a periphery, wherein said second structure comprises an outer side, wherein said apparatus further comprises catches, and supporting elements, wherein said catches bear against said outer side of said second structure, wherein said supporting elements are provided on said first structure, and wherein said periphery of said second structure bears against said supporting elements.

13. The apparatus of claim 1, further comprising an enclosure for defining said clean chamber and separating said clean chamber from surroundings thereof, wherein containers are aseptically treated within said enclosure, wherein said enclosure comprises a wall, and wherein said wall comprises said second structure.

* * * * *